(12) United States Patent
Reznik

(10) Patent No.: US 7,785,287 B2
(45) Date of Patent: Aug. 31, 2010

(54) ARTHROSCOPIC FLUID CONTROL DEVICE

(76) Inventor: Alan M. Reznik, 35 Overhill Rd., Woodbridge, CT (US) 06525

( * ) Notice: Subject to any disclaimer, the term of this patent is extended or adjusted under 35 U.S.C. 154(b) by 561 days.

(21) Appl. No.: 11/730,944

(22) Filed: Apr. 5, 2007

(65) Prior Publication Data

US 2007/0239113 A1 Oct. 11, 2007

Related U.S. Application Data

(60) Provisional application No. 60/789,598, filed on Apr. 6, 2006.

(51) Int. Cl.
*A61B 17/20* (2006.01)
(52) U.S. Cl. ................. 604/22; 604/30; 601/2
(58) Field of Classification Search ............ 137/625.37; 604/30, 96.01; 606/167, 49
See application file for complete search history.

(56) References Cited

U.S. PATENT DOCUMENTS

| | | | |
|---|---|---|---|
| 2,764,181 A | 9/1956 | Richolt | |
| 4,461,052 A | 7/1984 | Mostul | |
| 4,535,821 A * | 8/1985 | Anderson | 137/884 |
| 4,935,005 A * | 6/1990 | Haines | 604/30 |
| 4,940,457 A | 7/1990 | Olson | |
| 5,322,506 A | 6/1994 | Kullas | |
| 5,328,456 A * | 7/1994 | Horiguchi et al. | 604/22 |
| 5,484,402 A * | 1/1996 | Saravia et al. | 604/35 |
| 5,643,302 A | 7/1997 | Beiser et al. | |
| 5,810,770 A * | 9/1998 | Chin et al. | 604/65 |
| 5,944,054 A * | 8/1999 | Saieva | 137/625.4 |
| 6,602,221 B1 * | 8/2003 | Saravia et al. | 604/31 |
| 7,033,334 B2 * | 4/2006 | Samolyk | 604/6.01 |
| 2005/0283150 A1 * | 12/2005 | Moutafis et al. | 606/49 |
| 2007/0068573 A1 * | 3/2007 | Cox et al. | 137/1 |
| 2007/0202608 A1 * | 8/2007 | Uffenheimer et al. | 436/180 |

* cited by examiner

*Primary Examiner*—Nicholas D Lucchesi
*Assistant Examiner*—Ian K Holloway
(74) *Attorney, Agent, or Firm*—Hoffman, Wasson & Gitler, P.C.

(57) ABSTRACT

The fluid control device is attached to tubes carrying irrigation solution to form the system. The control device splits the flow through a fiber optic scope and a fluid control unit. The fluid control unit controls rate of flow and direction. The flow of fluid into the joint, out of the joint, or no flow is easily controlled by the operator. The device also allows more than one inflow, useful when using suction or suction shaving devices. The increased flow prevents collapse of a joint space and maintains clear visualization. The fluid flow relies on gravity by having a fluid reservoir positioned at a high point in the system.

5 Claims, 8 Drawing Sheets

ARTHROSCOPIC FLUID CONTROL DEVICE

This application claim benefit of provisional application 60/789,598, filed Apr. 6, 2006.

BACKGROUND OF THE INVENTION

During arthroscopic surgery the flow of fluids and suction to the site must be controlled based on the surgeon's needs. Normally, fluid control is achieved with the use of a mechanical pump. Mechanical pumps have high initial costs plus maintenance costs and there is always the possibility that, during surgery, a pump will fail. There is always a risk of electric conduction injury and a risk of compartment syndrome where fluid pressure in a compartment exceeds venous pressure causing a loss of circulation to a limb or muscle group. This risk can be even greater with some of the current mechanical fluid systems when fluid leaks into spaces outside the joint as occurs in acute trauma when there is communication between the joint and local soft tissue. The invention gravity controlled positive pressure, in combination with the various modes of flow, reduces this risk and can eliminate the need for a tourniquet, thereby also reducing tourniquet related injuries due to vascular compromise and post operative lactic acid accumulation in a limb.

There is a need in the art for a fluid control device not relying on a mechanical pump that provides adequate flow, control of direction of the flow and control of the flow rate.

Existing electromechanical system are based on constant pressure or constant flow. The invention has distinct advantages over such a system because it only replenishes fluid that flows out of the joint, decreasing the amount of soft tissue swelling during the course of the procedure. Also, the gravity based system creates positive pressure environment in the joint to decrease intraarticular bleeding. Also, the system has multiple modes of flow allowing for more ways to clear intraarticular debris in the joint.

SUMMARY OF THE INVENTION

The fluid control device is attached to tubes carrying irrigation solution to form the system. The control device splits the flow through a fiber optic scope and a fluid control unit. The fluid control unit controls rate of flow and direction. The flow of fluid into the joint, out of the joint, or no flow is easily controlled by the operator. The device also allows more than one inflow, useful when using suction or suction shaving devices. The increased flow prevents collapse of a joint space and maintains clear visualization. The fluid flow relies on gravity by having a fluid reservoir positioned at a high point in the system.

DETAILED DESCRIPTION OF THE INVENTION

Figure 1:
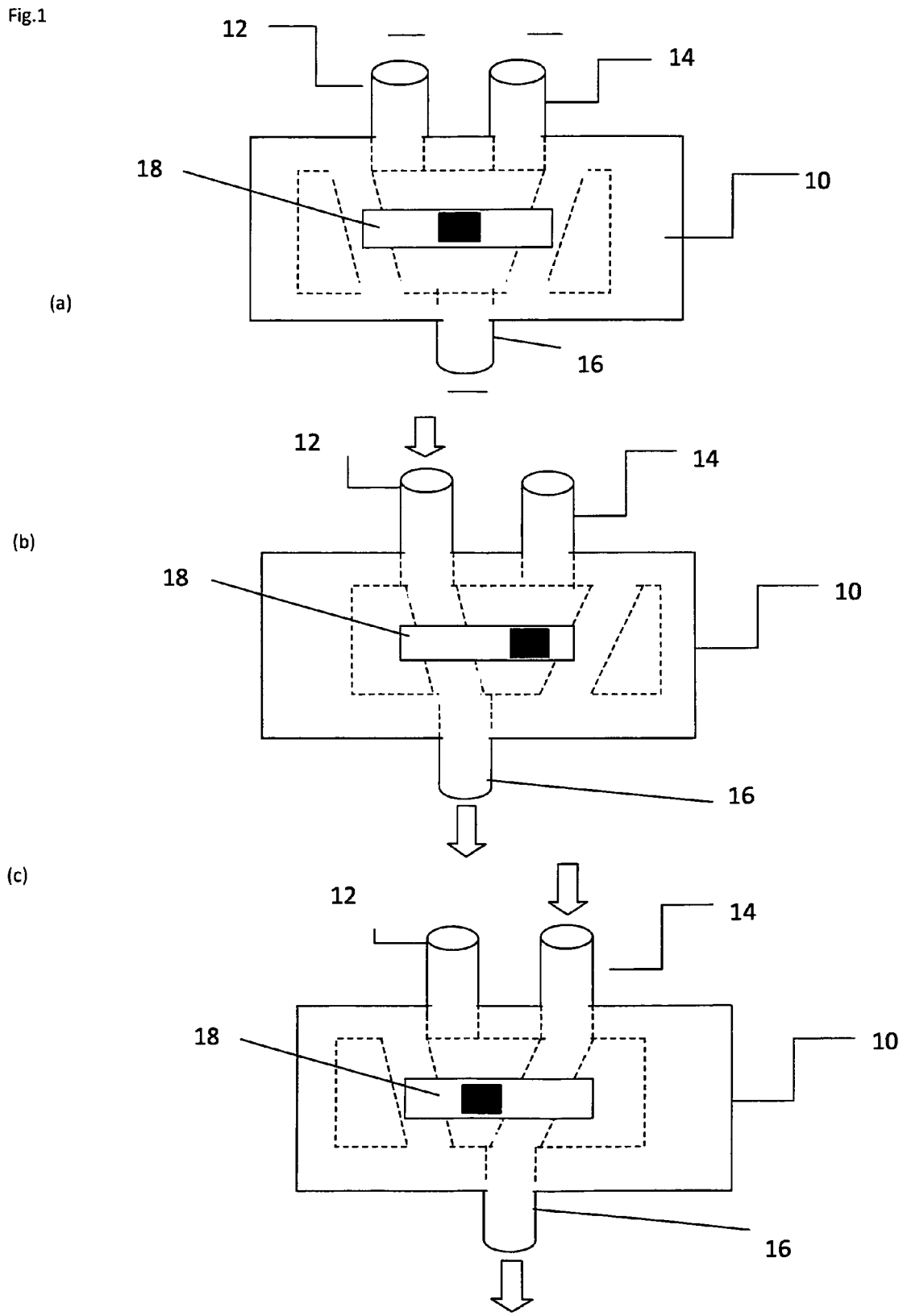
FIG. 1 shows the fluid control device in each of three positions.

FIG. 1 shows a fluid control device 10 having three ports 12, 14, 16. A slider is positioned between the two ports 12, 14. In FIG. 1A, the slider 18 is in the central position and there is no fluid communication between any ports. In FIG. 1B, the slider is moved to the right position and fluid flows between ports 12 through port 16. In FIG. 1C, a slider is moved to the left position and there is fluid communication between the port 16 and port 14.

Figure 2:
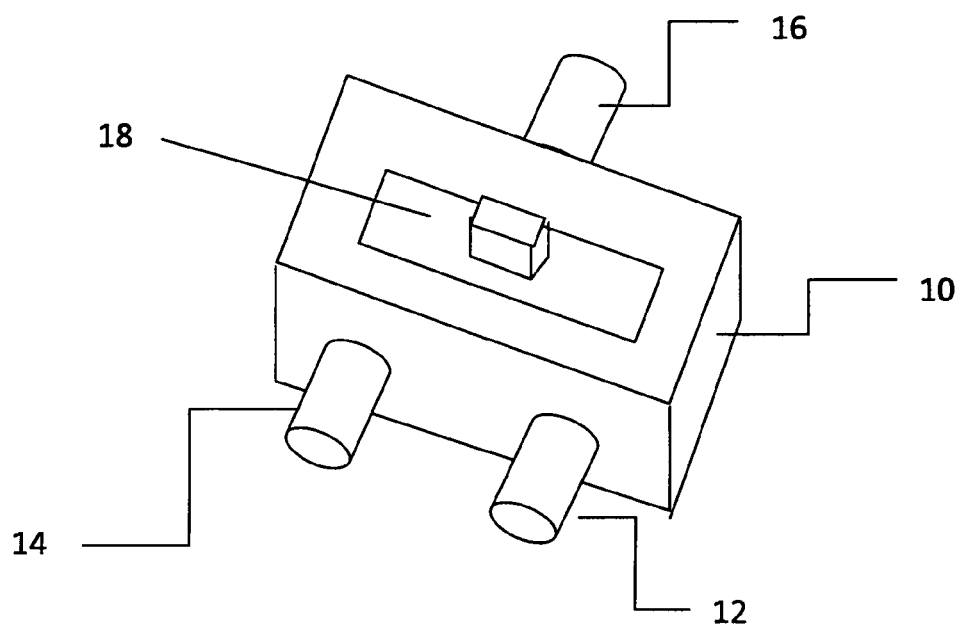
FIG. 2 shows views of the fluid control device.

FIG. 2 shows the front rear end perspective view of the fluid control device. In the front view, the slider and port 16 are seen. In the rear view, the ports 12 and 14 are seen, as well as the slider. This perspective view shows all three ports 12, 14, 16 and the slider 18.

Figure 3:
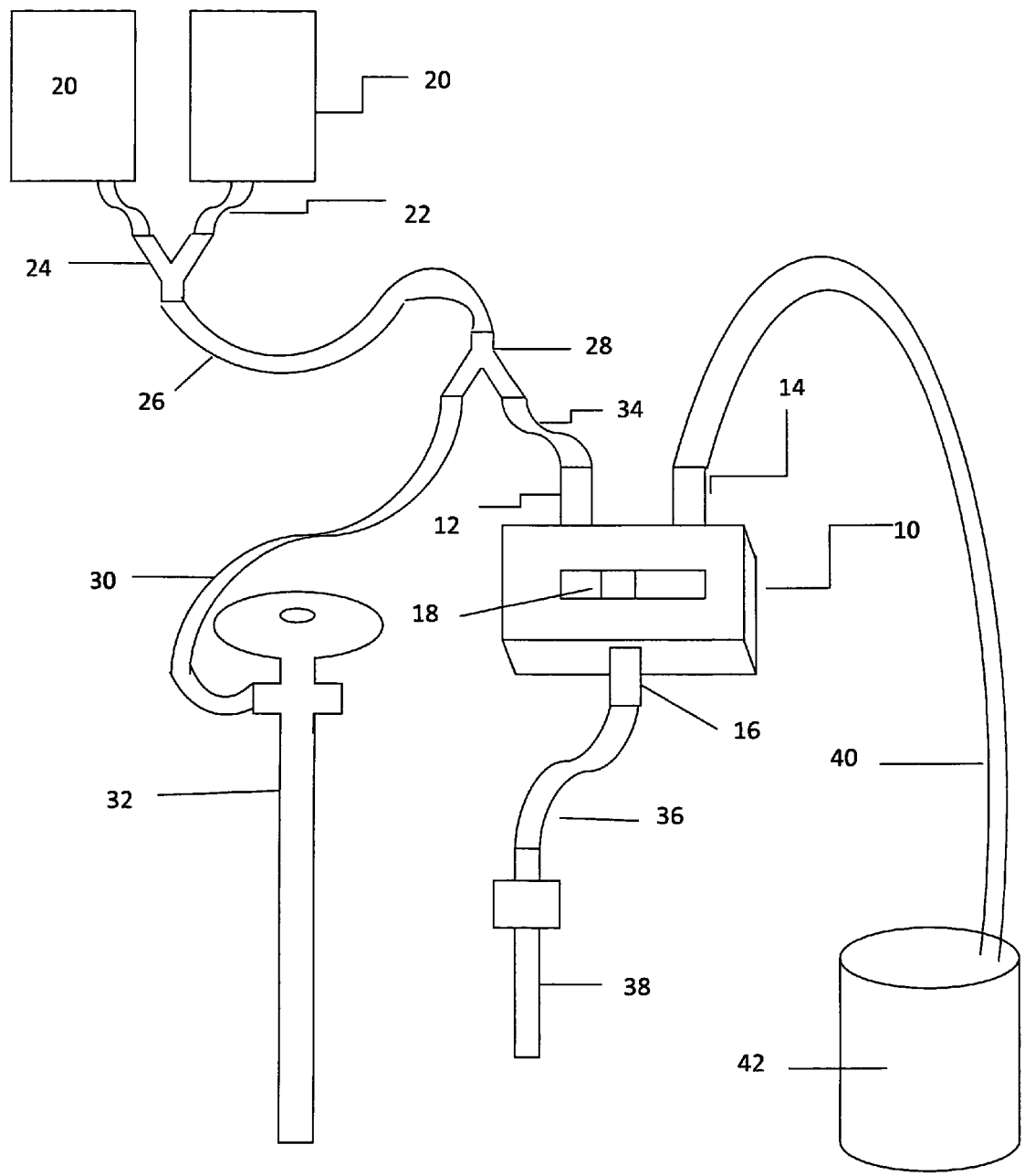
FIGS. 3-8 show the system in various modes used during surgery.

FIG. 3 shows the complete fluid control system, with fluid reservoirs 20 each having an outlet line 22 connected to a fluid divider, such as a Y junction 24, with line 26 leading from the Y junction 24 to a second Y junction 28. A single reservoir may be used which would be connected to the line 26. A first line 30 leads from the Y junction 28 to an arthroscope 32. A second line 34 extends from the Y junction 28 to the port 12 on the fluid control device 10. Leading from the port 16 is a line 36 terminating in a flow port cannula 38. A drain line 40 is connected to port 14 and leads to a gravity drainage 42.

Figure 4:
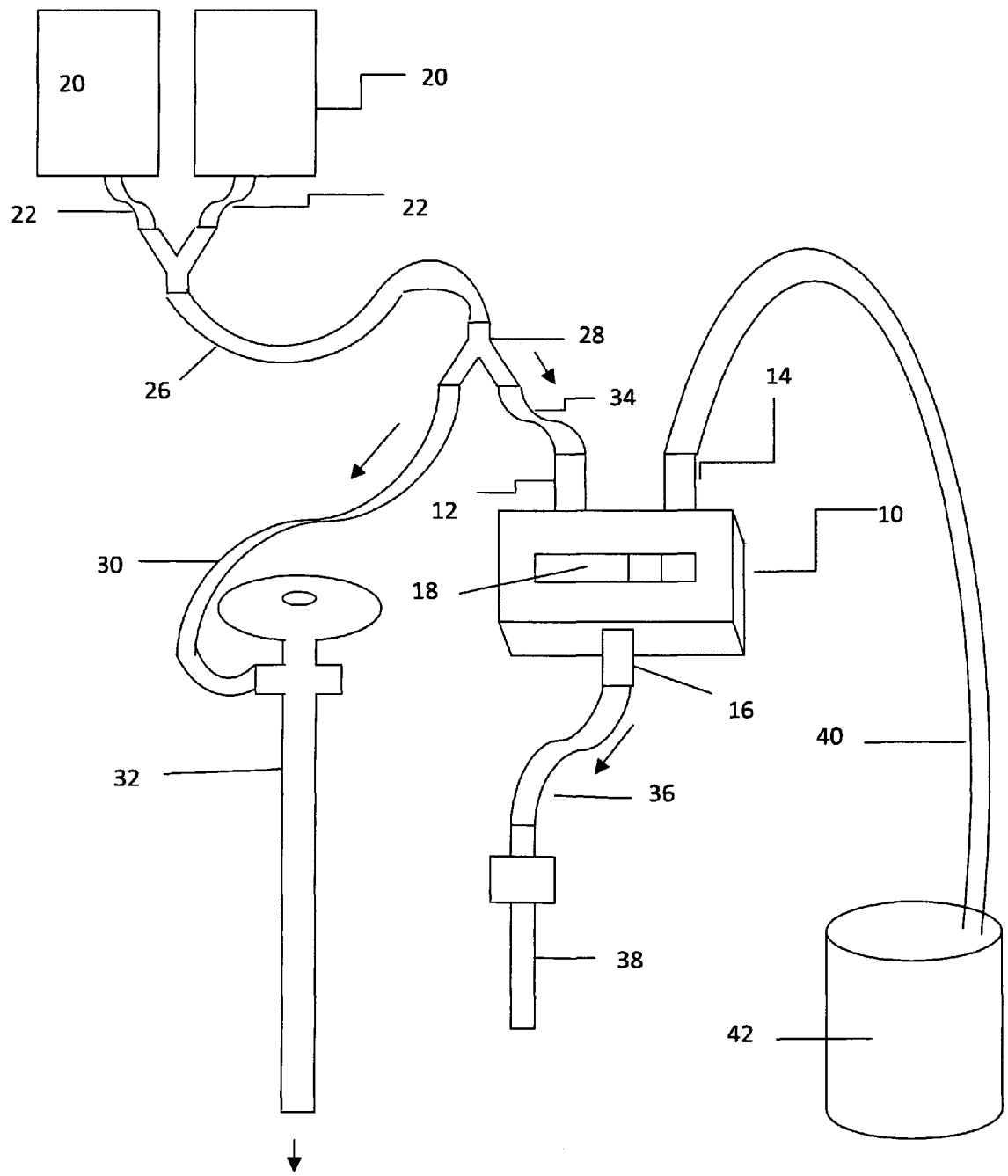
Figure 5:
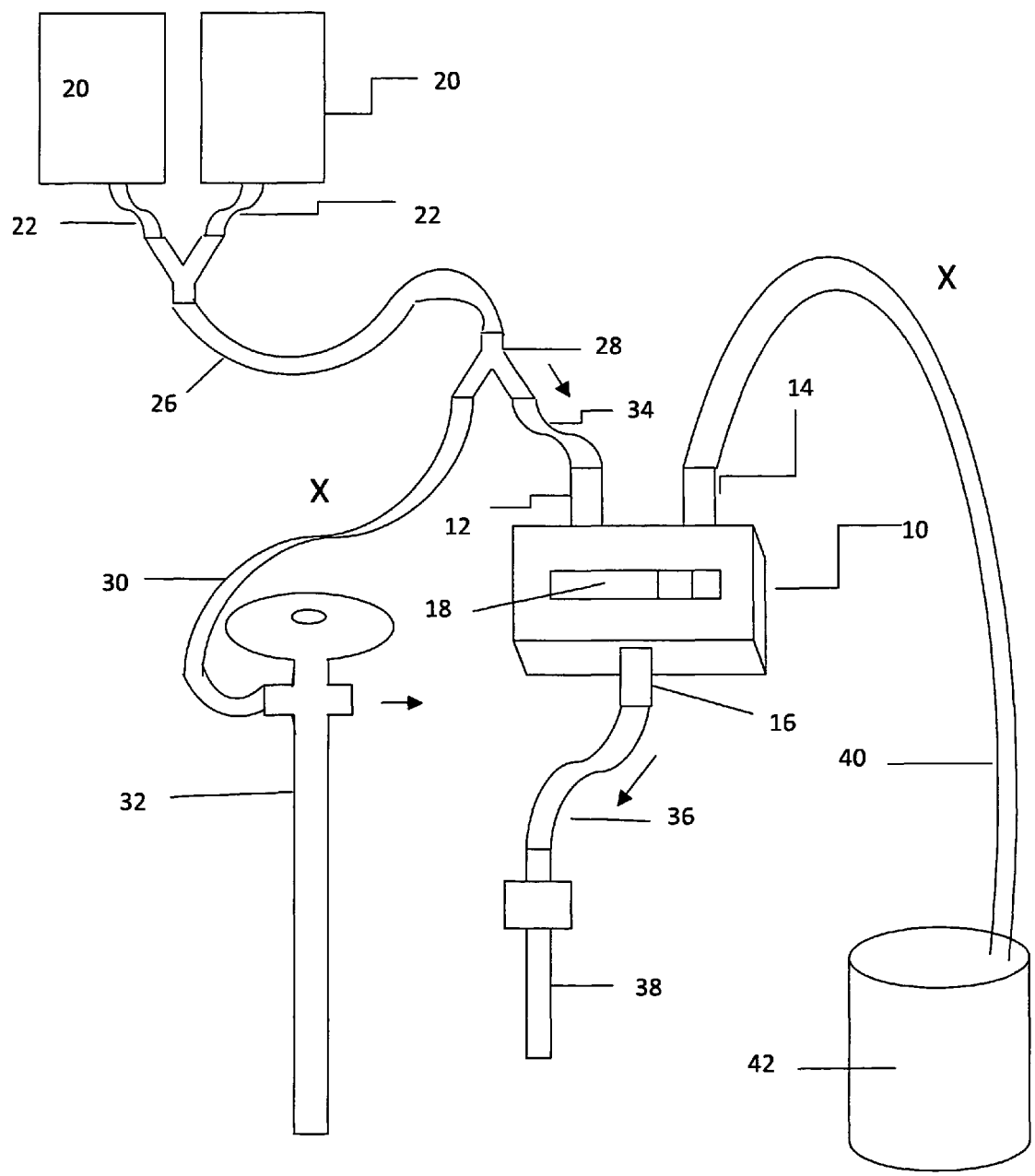
Figure 6:
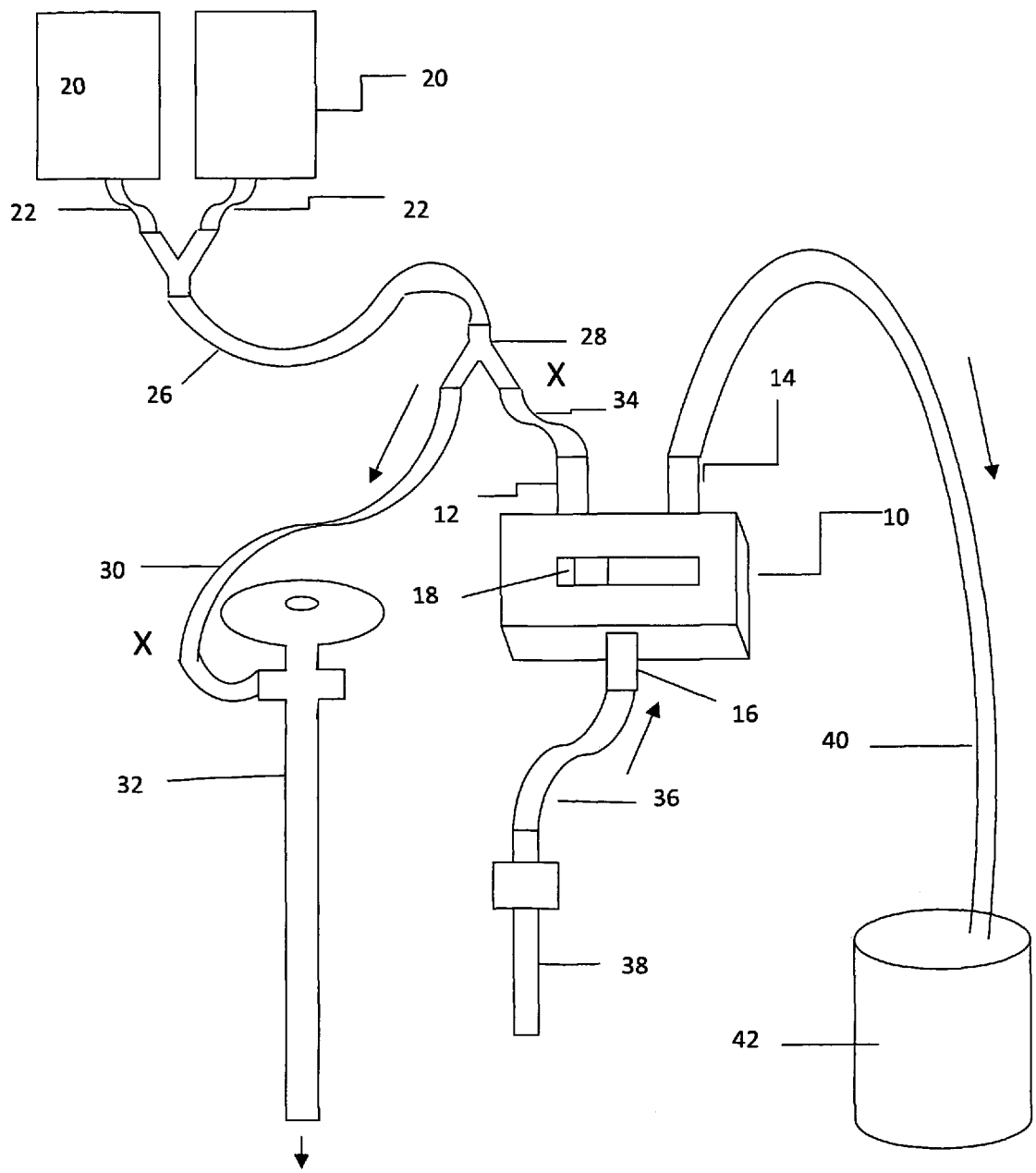
Figure 7:
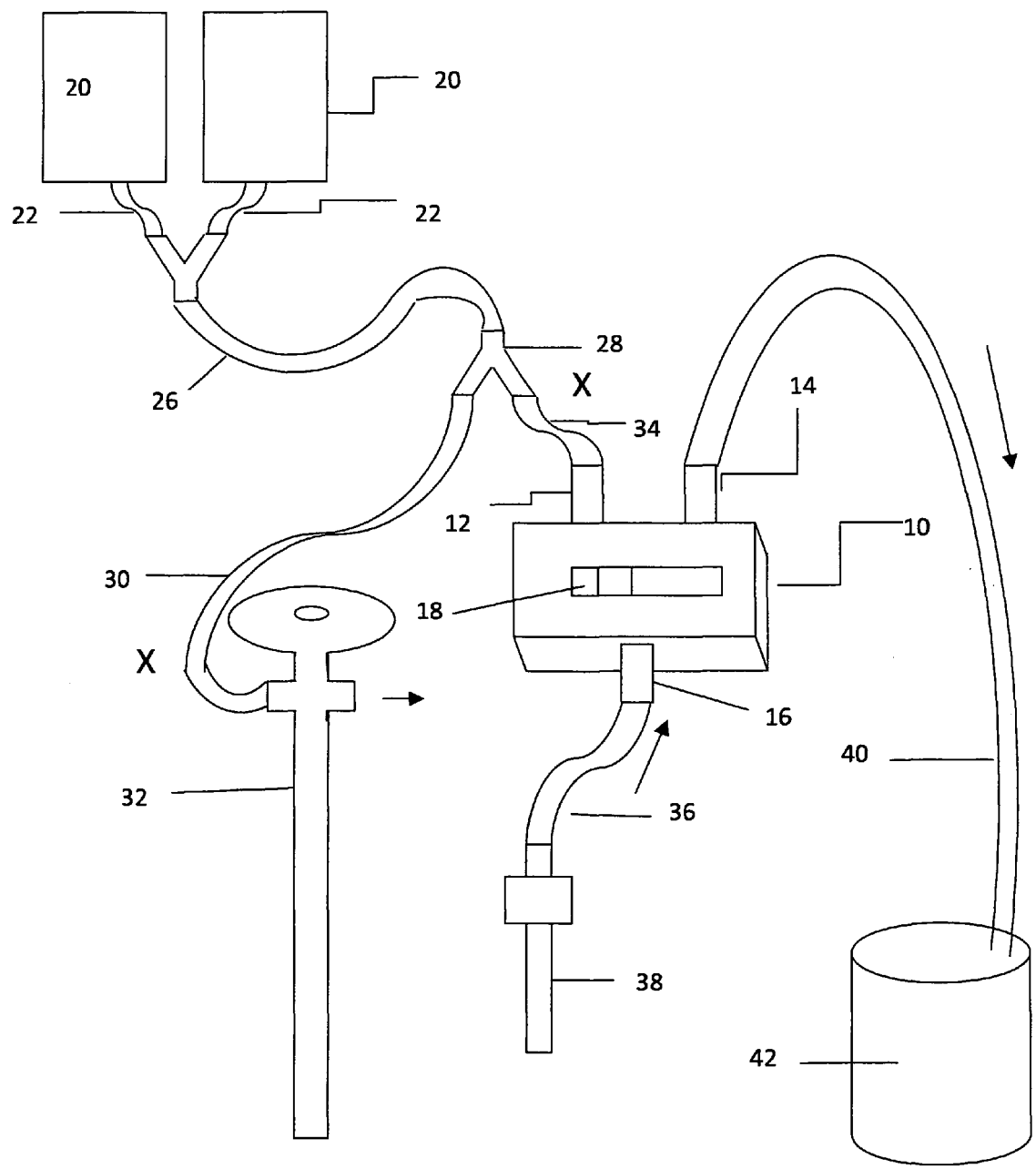
Figure 8:
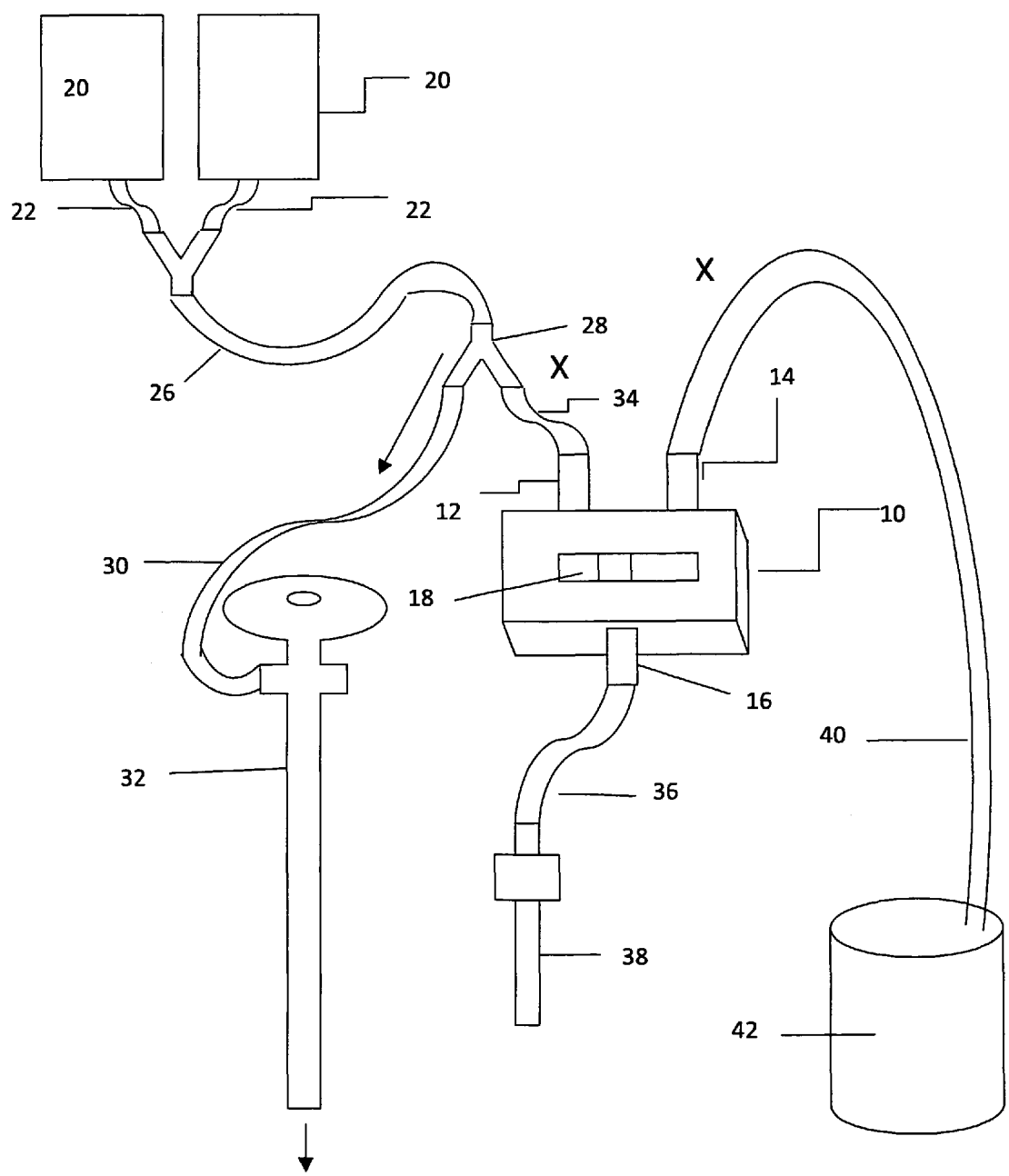

The various modes of operation of the system, including the control device 10, are seen in FIGS. 4-8. FIG. 4 shows a dual inflow operation with flow extending through ports 12 and out port 16 to the flow port cannula 38 and also having fluid flow through the arthroscope 32. The slider is moved to the right. In FIG. 5, the slide 18 is moved to the right allowing fluid flow into port 12 and out port 16 but fluid flow through the arthroscope exits out the side ports of the scope sheath. In FIG. 6 the slide 18 is moved to the left and fluid flows from the reservoir to the arthroscope 32 and drainage fluid flows up through port 16 and out port 14 to the drainage 42. In FIG. 7, the slide is moved to the left and fluid flow through the arthroscope exits the side port of the scope sheath, but fluid extends up through the flow port cannula into port 16 and out port 14, eventually to the suction drainage 42. Lastly, in FIG. 8, the slide 18 is in the middle position and fluid from the reservoir extends only through the arthroscope with no flow of fluid through the device 10.

The device allows fluid flow to be easily altered to meet the current demand, using no other driving force than gravity, although a pump could be used in conjunction with the system.

While the invention has been described with reference to a preferred embodiment, variations and modifications would be apparent to one of ordinary skill in the art. The invention encompasses such variations and modifications.

I claim:

1. A pump and vacuum free arthroscopic fluid flow device for controlling fluid flow rate and direction into and out of a joint comprising at least one fluid reservoir, a first conduit extending from said at least one fluid reservoir, wherein the first conduit has a Y-junction, a first and second line extending from the Y-junction, the first line leads from the Y-junction to an arthroscope, a pump and vacuum free fluid rate and flow direction controller, the fluid rate and flow direction controller having a first port, a second port and a third port, the second line of the first conduit extending between the Y-junction and the fluid rate and flow direction controller first port, a second conduit extending from the fluid rate and flow and direction controller second port and having a fluid port cannula attached to the second conduit, a third conduit extending from the fluid rate and flow controller second port, the third conduit connected to gravity drainage, the fluid rate and flow direction controller comprised of a slider device movable between three positions and having a first mode when the slider is placed in a first position allowing fluid flow between the first conduit and the second conduit and preventing fluid flow from the second conduit to the third conduit: a second mode when the slider is placed in a second position allowing fluid flow from the second conduit to the third conduit and preventing fluid flow from the first conduit to the second conduit or a third mode when the slider is placed in a third position preventing all fluid flow through the fluid controller.

2. The fluid device of claim 1, further comprising a drainage line connected to the third conduit.

3. A method of controlling the fluid flow rate into and out of a joint during an arthroscopic procedure comprising the steps of adjusting the fluid flow rate into and our of the joint using the device as claimed in claim 1, without a pump or vacuum.

4. The method of claim 3, wherein outgoing fluid flowing into the drainage line is caused by gravity or a positive pressure environment in the joint.

5. The method of claim 3, wherein the fluid rate and flow direction controlling slider device is placed in a position between the first position, the second position, and the third position allowing partial flow in either direction through the flow direction controller.

* * * * *